United States Patent
Chmielewski et al.

(10) Patent No.: US 10,898,096 B2
(45) Date of Patent: Jan. 26, 2021

(54) APPARATUS AND METHOD FOR CONNECTING ELEMENTS IN MEDICAL DEVICES

(71) Applicant: St. Jude Medical, Cardiology Division, Inc., St. Paul, MN (US)

(72) Inventors: David Chmielewski, Lakeville, MN (US); Terry Sterrett, Huntington Beach, CA (US); Kevin C. Flinn, Newport Beach, CA (US); Andy H. Do, Garden Grove, CA (US); Allyn Jensrud, Burnsville, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 792 days.

(21) Appl. No.: 14/919,354

(22) Filed: Oct. 21, 2015

(65) Prior Publication Data

US 2016/0114132 A1  Apr. 28, 2016

Related U.S. Application Data

(60) Provisional application No. 62/069,119, filed on Oct. 27, 2014.

(51) Int. Cl.
*A61B 5/042* (2006.01)
*A61B 18/00* (2006.01)
(Continued)

(52) U.S. Cl.
CPC .......... *A61B 5/0422* (2013.01); *A61B 5/6857* (2013.01); *A61B 18/1492* (2013.01); *A61M 39/14* (2013.01); *A61B 2018/00351* (2013.01); *A61B 2018/00839* (2013.01); *A61B 2018/1407* (2013.01); *A61B 2018/1435* (2013.01);
(Continued)

(58) Field of Classification Search
CPC .... A61B 2017/003; A61B 2017/00318; A61B 2017/00323; B21F 15/00; B21F 15/02; B21F 15/04; B21F 15/06; B21F 15/08
USPC ................ 600/372–375, 377, 380, 381, 393, 600/508–509; 606/20–42; 607/115–116, 607/119–127, 129, 131; 140/111–118
See application file for complete search history.

(56) References Cited

U.S. PATENT DOCUMENTS 4,799,474 A * 1/1989 Ueda .................... A61B 1/0058
600/133
5,031,636 A * 7/1991 Gambale ........... A61M 25/0169
600/585

(Continued)

FOREIGN PATENT DOCUMENTS

GB     103701    *  2/1917
GB     124320    *  3/1919

*Primary Examiner* — Joseph A Stoklosa
*Assistant Examiner* — Brian M Antiskay
(74) *Attorney, Agent, or Firm* — Dykema Gossett PLLC

(57) ABSTRACT

A connection device for a deflectable medical device, such as a catheter, comprises an elongate planarity wire having a proximal end and a distal end, an elongate activation wire having a proximal end a distal end, a passage and an interface. The passage extends through the planarity wire near the distal end of the planarity wire. The distal end of the activation wire extends through the passage. The interface is between the passage and the activation wire, and may comprise one or more of the following: a hook and bore interface, a detent interface, a mechanical interface, or a metallurgical interface.

10 Claims, 11 Drawing Sheets

(51) Int. Cl.
  *A61M 25/01* (2006.01)
  *A61M 39/14* (2006.01)
  *A61B 18/14* (2006.01)
  *A61B 5/00* (2006.01)

(52) U.S. Cl.
  CPC ............... *A61B 2018/1467* (2013.01); *A61M 2025/015* (2013.01)

(56) References Cited

U.S. PATENT DOCUMENTS

| | | | | |
|---|---|---|---|---|
| 5,246,445 A * | 9/1993 | Yachia | ...................... | A61F 2/88 604/104 |
| 5,304,219 A * | 4/1994 | Chernoff | ................ | A61N 1/056 439/669 |
| 5,308,324 A * | 5/1994 | Hammerslag | ..... | A61M 25/0144 600/585 |
| 5,480,382 A * | 1/1996 | Hammerslag | ..... | A61M 25/0053 600/585 |
| 5,487,757 A * | 1/1996 | Truckai | .............. | A61B 18/1492 604/264 |
| 5,685,878 A * | 11/1997 | Falwell | .............. | A61B 18/1492 600/372 |
| 5,827,278 A * | 10/1998 | Webster, Jr. | ........ | A61B 18/1492 606/41 |
| 6,287,301 B1 * | 9/2001 | Thompson | ......... | A61B 18/1492 604/524 |
| 6,949,099 B2 * | 9/2005 | Shiro | ..................... | A61B 18/14 606/45 |
| 9,387,034 B2 * | 7/2016 | Okada | .................... | A61B 18/14 |
| 2002/0177766 A1 * | 11/2002 | Mogul | ................. | A61B 5/0422 600/374 |
| 2004/0143257 A1 * | 7/2004 | Fuimaono | .......... | A61B 18/1482 606/41 |
| 2005/0131343 A1 * | 6/2005 | Abrams | ............ | A61M 25/0662 604/95.04 |
| 2005/0215996 A1 * | 9/2005 | Ouchi | ............ | A61B 17/320016 606/46 |
| 2005/0272975 A1 * | 12/2005 | McWeeney | ........ | A61B 1/00071 600/113 |
| 2005/0288656 A1 * | 12/2005 | Koerner | ................. | A61B 18/02 606/21 |
| 2007/0299424 A1 * | 12/2007 | Cumming | ......... | A61M 25/0012 604/527 |
| 2008/0097298 A1 * | 4/2008 | Fisher | ............ | A61B 17/320758 604/103.04 |
| 2008/0139999 A1 * | 6/2008 | Gibson | ............. | A61M 25/0041 604/95.04 |
| 2010/0030114 A1 * | 2/2010 | Nguyen | ............ | A61M 25/0043 600/585 |
| 2010/0280449 A1 * | 11/2010 | Alvarez | ........... | A61B 17/00234 604/95.04 |
| 2012/0116199 A1 * | 5/2012 | de la Rama | ......... | A61B 5/0422 600/374 |
| 2013/0053844 A1 * | 2/2013 | Suzuki | ............... | A61B 18/1445 606/46 |
| 2013/0281925 A1 * | 10/2013 | Benscoter | .......... | A61B 1/0125 604/95.04 |

* cited by examiner

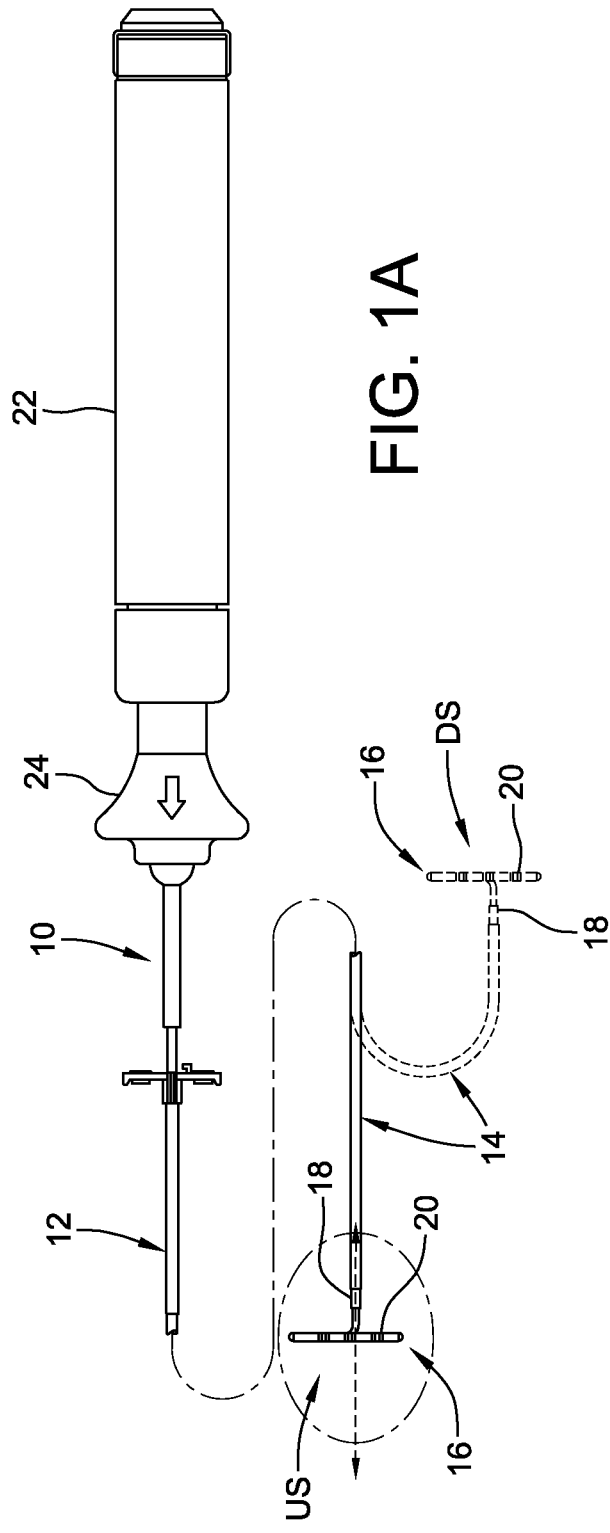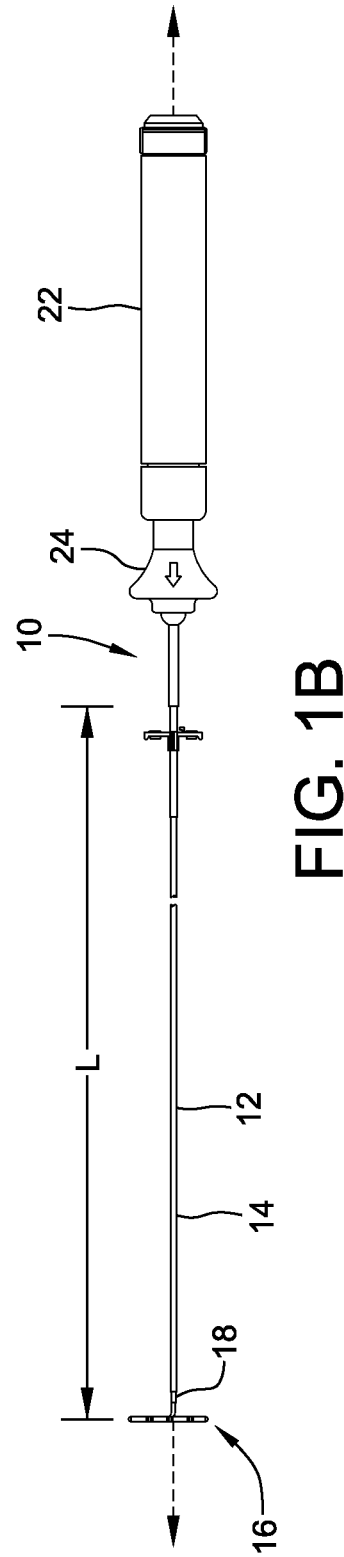

APPARATUS AND METHOD FOR CONNECTING ELEMENTS IN MEDICAL DEVICES

CROSS-REFERENCE TO RELATED APPLICATIONS

This application claims the benefit and priority to U.S. provisional patent application No. 62/069,119, filed 27 Oct. 2014, which is hereby incorporated by reference as though fully set forth herein.

BACKGROUND a. Field

The present disclosure generally relates to medical devices configured for diagnosis or treatment of tissue within a body. In particular, the disclosure relates to connection devices used in deflectable medical devices, such as electrophysiology (EP) catheters.

b. Background Art

Catheters are used for an ever-growing number of procedures. For example, catheters are used for diagnostic, therapeutic, and ablative procedures, to name just a few examples. Typically, the catheter is manipulated through the patient's vasculature and to the intended site, for example a site within the patient's heart.

A typical EP catheter includes an elongate shaft and one or more electrodes on the distal end of the shaft. The electrodes can be used for ablation, diagnosis, or the like. Oftentimes, these electrodes are ring electrodes that extend about the entire circumference of the catheter shaft.

One specific use of an EP catheter is to map the atrial regions of the heart, and in particular the pulmonary veins, which are often origination points or foci of atrial fibrillation. Such EP mapping catheters may have at least a partial loop-shape at their distal end in order to surround the ostium of a pulmonary vein. Because of varying patient anatomies, however, it can be challenging to properly place the looped section of the catheter precisely in the pulmonary vein ostia.

Some catheters are deflectable so as to be able to reach different locations within the anatomy of the patient. For example, upon the application of a force to an activation wire at the catheter handle, the catheter shaft can be deflected to displace the distal portion of the shaft. Some catheters employ flat wires in an attempt to limit deflection to within a single plane.

It can sometimes be a challenge to provide adequate connection strength between various components within the limited space of a catheter shaft using conventional methods such as soldering. In one design, a nitinol wire is joined to a 300-series stainless steel tube via crimping before being metallurgically connected to the flat wire. Such a design is useful in joining dissimilar metals that cannot be connected via brazing, but does little to improve connection between components of dissimilar geometry, such as flat and round elements.

BRIEF SUMMARY

The present disclosure is directed to systems and methods for connecting members in medical devices. In one embodiment, a connection device for a deflectable medical device, such as a catheter, comprises an elongate planarity wire having a proximal end and a distal end, an elongate activation wire having a proximal end a distal end, a passage and an interface. The passage extends through the planarity wire near the distal end of the planarity wire. The distal end of the activation wire extends through the passage. The interface is between the passage and the activation wire, and may comprise one or more of the following: a hook and bore interface, a detent interface, a mechanical interface, or a metallurgical interface.

In another embodiment, a medical device is configured for diagnosis or treatment of tissue within a body. The medical device comprises an elongate, deformable member, an operational element, a flat wire, an activation wire and a connection device. The elongate, deformable member has a proximal end and a distal end. The elongate, deformable member defines a lumen extending axially between said proximal and distal ends. The operational element couples to a distal region of said elongate, deformable member. The flat wire extends within said lumen. The activation wire extending within said lumen from said proximal end to said flat wire. The connection device joins the flat wire and the activation wire. The connection device comprises a passage through the flat wire and in which the activation wire is disposed, and a bonding agent joining the activation wire to the flat wire at the passage.

In another embodiment, a method for manufacturing a connection device between a flat wire and a round wire in a medical device comprises forming a passage within a flat wire, feeding a round wire through the passage, and forming an interface between said passage and said round wire.

BRIEF DESCRIPTION OF THE DRAWINGS

FIG. 1A is a plan view of an exemplary catheter having a shaft including a distal loop region and a proximal handle region, the plan view illustrating the shaft in both a deflected and an un-deflected state.

FIG. 1B is a plan view of the exemplary catheter shown in FIG. 1A illustrating the shaft in an un-deflected state.

DETAILED DESCRIPTION

Figure 2A:
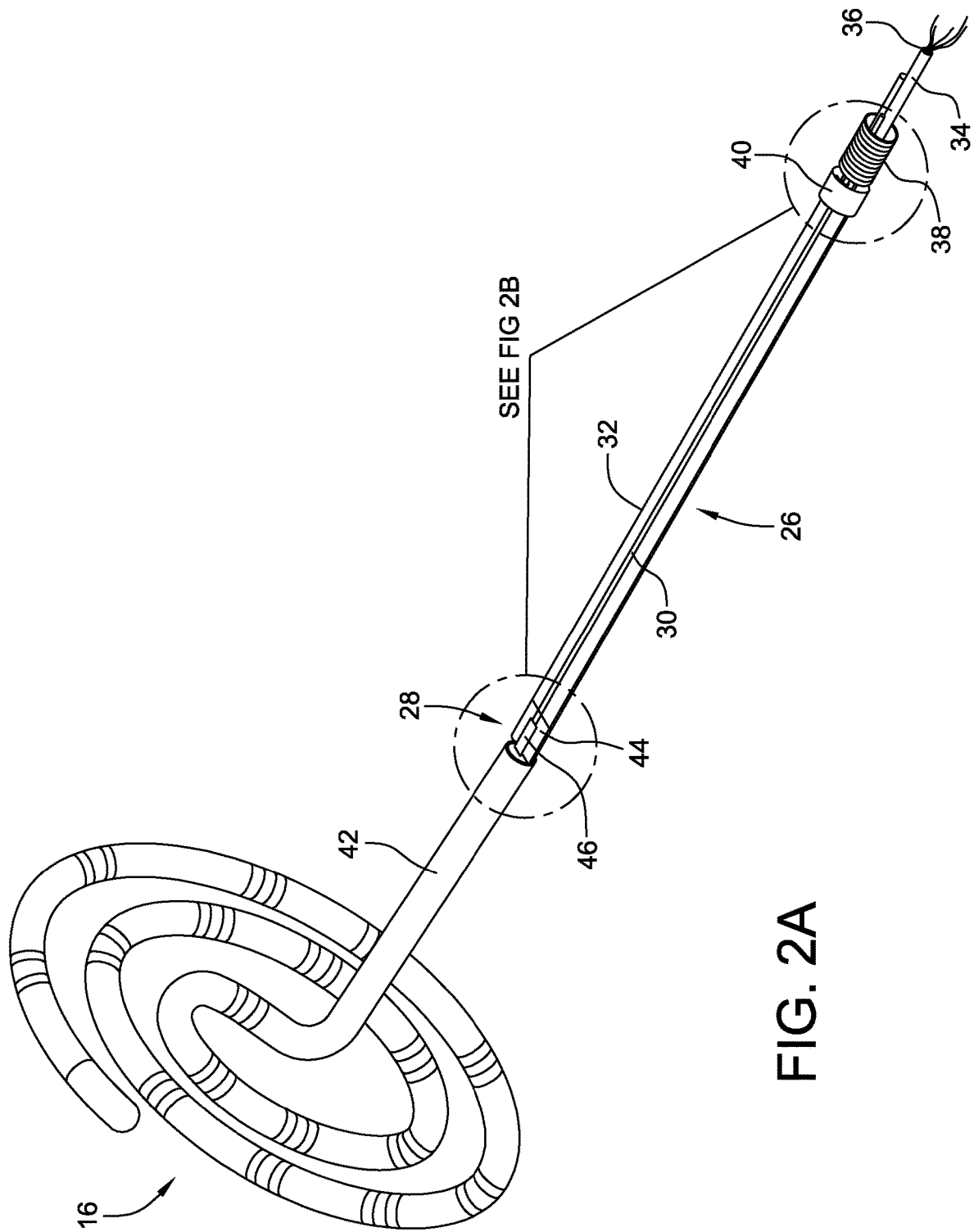
FIG. 2A is a perspective view of the distal loop region of the shaft of FIGS. 1A and 1B showing a flat wire and an activation wire of a flat wire assembly.

FIG. 1A is a plan view of an exemplary catheter 10 having shaft 12 including a proximal shaft region 14 and distal loop region 16. In FIG. 1A, shaft 12 is illustrated in both a deflected and an un-deflected state (denoted as "US" and "DS" respectively). Shaft 12 additionally includes neck region 18 and electrodes 20. Catheter 10 additionally includes handle 22 and push-pull handle 24. FIG. 1B is a plan view of the exemplary catheter 10 illustrated in FIG. 1A in an un-deflected state (i.e., state "US" of FIG. 1A). FIGS. 1A and 1B are discussed concurrently. Proximal shaft region 14 is disposed near handle 22—in close proximity to where an operator of catheter 10 would manipulate the device, while distal shaft region 16 extends away from handle 22 and proximal shaft region 14—distal to where an operator of catheter 10 would manipulate the device. It should be noted that the particular distal shaft shape, electrode configuration, shaft deflection shapes, deflection actuators, handles, and other catheter components shown in FIGS. 1A and 1B are depicted for purposes of example only. The principles described herein are equally applicable to connecting elements subject to forces, such as tensile forces, in these and other medical devices having different distal shaft shapes, electrode configurations, shaft deflection shapes, deflection actuators, handles, etc.

In use, a distal portion of a catheter may be introduced into a patient's body proximate an area of interest, such as distal loop region 16 of EP catheter 10 into a pulmonary vein ostium. Electrodes 20 can then be employed for diagnostic or therapeutic purposes. At the proximal end of catheter shaft 12, a plurality of individually electrically insulated elongate conductors (see conductors 34 of FIGS. 2A & 2B) emerge and are adapted to be individually coupled to a mass termination terminal within handle 22 for ultimate electrical communication with an EP recording system, an electroanatomical localization and visualization system (e.g., such as the ENSITE system of St. Jude Medical, Inc. operating the ONEMAP facility or other similar systems for monitoring cardiac activity and providing one or more visual representations of same).

One or more activation wires (see activation wire 30 of FIGS. 2A-2C) can be actuated using push-pull handle 24 in order to deflect proximal shaft region 14 of catheter shaft 12 such that distal region 16 is oriented generally towards an area of interest, such as an ostium. In other words, the representative distal loop region 16 can be deflected toward proximal shaft region 14 for some distance, such as, approximately one-hundred-eighty degrees. In the illustrated example, the activation wire couples to a flat wire assembly such that forces are transferred to shaft 12 proximal of distal loop region 16 (and neck region 18) via a deflection mechanism activated by push-pull handle 24. Using the connection devices described herein, the activation wire bends a flat wire to deflect shaft 12 in a common plane. The connection devices provide adequately strong couplings between the flat wire and the activation wire.

Catheter shaft 12, in some embodiments, is tubular so as to define at least one lumen therethrough in which the connection devices and flat wire assembly described herein are located. One of ordinary skill in the art will appreciate that the relative lengths of proximal shaft region 14, distal loop region 16, and neck region 18 depicted in FIGS. 1A and 1B are merely illustrative and can vary without departing from the spirit and scope of the present disclosure but likely should not have a magnitude of less than about 110 cm. Of course, the overall length L of catheter body 12 should be long enough to reach the intended destination within the body of the patient. Catheter shaft 12 will typically be made of a biocompatible polymeric material, such as polytetrafluoroethylene (PTFE) tubing (e.g., TEFLON® brand tubing). Of course, other polymeric materials or thermoplastics, can be utilized. In another embodiment, shaft 12 is made from polyamide-based thermoplastic elastomers (namely poly(ether-block-amide), such as PEBAX®). It is also contemplated that the durometer of catheter shaft 12 can vary along its length. In general, the basic construction of catheter shaft 12 will be familiar to those of ordinary skill in the art, and thus will not be discussed in further detail herein.

In an embodiment, distal loop region 16 has an outer-loop diameter of in the range of about 20 mm to about 35 mm, although other dimensions are not excluded. In the embodiments depicted herein the diameter of the outer loop of distal loop region 16 is fixed (e.g., at about 20 mm or less to about 33 mm or more, if desired) although using reasonably well-known techniques the diameter can be manually varied with one or more tension elements for imparting and releasing tension.

The outer diameter of catheter shaft 12 (expressed in units known as French abbreviated as "F", each unit of which equals ⅓ of a millimeter) can vary. For example, a majority of catheter shaft 12, including proximal shaft region 14, can be on the order of about 7 F and adjacent neck region 18 can include structure or shaping that transitions the outer diameter to about 4 F such that distal loop region 16 is 4 F or some other uniform outer diameter throughout. Neck region 18 may also include components, such as the connection devices, for anchoring the activation wire so as to cause deflection at the anchoring location proximal of distal loop region 16. Although, the connection devices may be located at any location along the length of catheter shaft 12 in other embodiments.

In one embodiment, distal loop region 16 includes nineteen 1 mm (wide) platinum ring-type electrodes 20 and a single 2 mm (long) tip electrode. Electrodes 20 can be spaced apart in bipolar pairs, evenly along a length of distal loop region 16, or in varying patterns. The lateral edges of electrodes 20 are bonded to the adjacent relatively smaller (e.g., 4 F) diameter biocompatible tubing (e.g., PTFE or the like) of distal loop region 16 with a biocompatible material such as a polyurethane matrix composed of Polycin 936 and Vorite 689 (mixed 52:48 percent, as an example) produced by CasChem Inc. of Bayonne, N.J.

In a bipolar pair configuration the electrode pair spacing can vary from about 2.5 mm to about 7 mm between pairs, with approximately 1 mm spacing within each bipolar pair, including a tip and ring pair. Such closely spaced bi-polar pairs tend to reduce so-called far field effects in an inchamber electrocardiogram (EGM) signal. In evenly spaced configurations, electrodes can be spaced anywhere from about 1 mm to about 7 mm, or some other nominal spacing between them. Irregularly spaced electrodes can be configured in a 1-7-1 configuration (that is, a 1 mm spacing could be followed by a 7 mm spacing followed by a 1 mm spacing), or some other pattern, with the tip electrode having some other spacing such as 2 mm.

In addition, a variety of localization, visualization, and/or orientation-specific elements can be incorporated into proximal shaft region 14, distal loop region 16, and neck region 18, such as metallic coil members, active impedance emitting or receiving electrodes, fluoroscopically opaque materials, and the like, for use in conjunction with an electroanatomical system, for example.

The present disclosure is described with reference to an EP catheter utilized in cardiac EP studies, such as the AFocus II DL (or dual loop) diagnostic catheter of St. Jude Medical, Atrial Fibrillation Division, Inc., which can provide relatively faster cardiac activity data collection having the necessary detail to efficiently diagnose complex cardiac arrhythmias. It should be understood, however, that the present teachings can be applied to good advantage in other contexts as well, such as radiofrequency (RF) ablation catheters or other diagnostic cardiac catheters.

As mentioned above, shaft 12 contains a flat wire assembly (see flat wire assembly 26 in FIGS. 2A-2C) that includes a connection device (see connection device 28 of FIGS. 3 & 4) that securely joins activation wire 30 to flat wire 32.

FIG. 2A is a perspective view of distal loop region 16 of shaft 12 of FIGS. 1A and 1B showing flat wire 32 and activation wire 30 of flat wire assembly 26. Tube 34, in which conductors 36 are located, extends through extended braid/spring subassembly 38 and tube 40, and underneath flat wire 32 to distal loop region 16. Likewise, activation wire 30 extends from handle 22 (FIG. 1A) through extended braid/spring subassembly 38 and tube 40, and atop flat wire 32 to connection device 28 just proximal of distal loop region 16. Connection device 28 includes soldering 44, to which tube 46 is connected to join loop wire 48 (FIG. 2B) to flat wire 32.

Figure 2B:
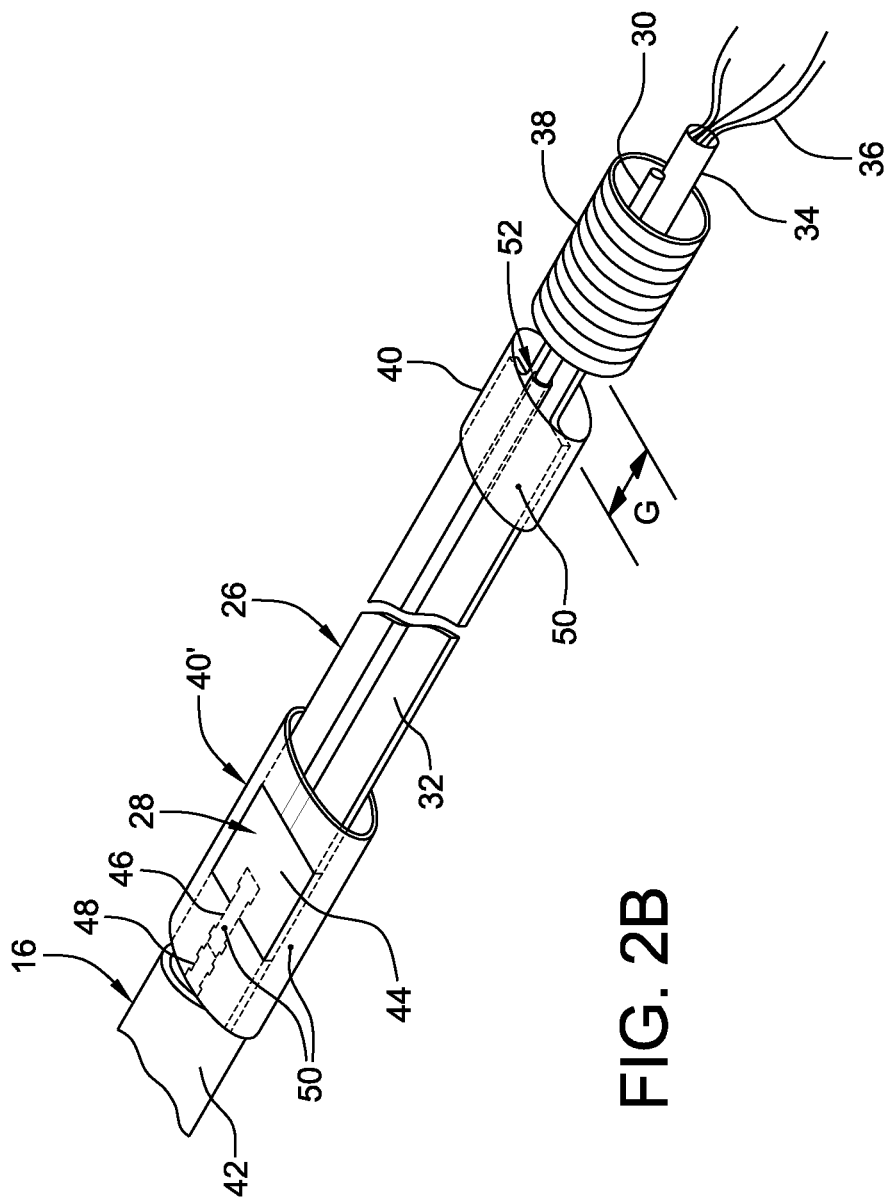
FIG. 2B is a fragmented perspective view of the flat wire assembly of FIG. 2A showing the flat wire linking the activation wire and a loop wire.
Figure 2C:
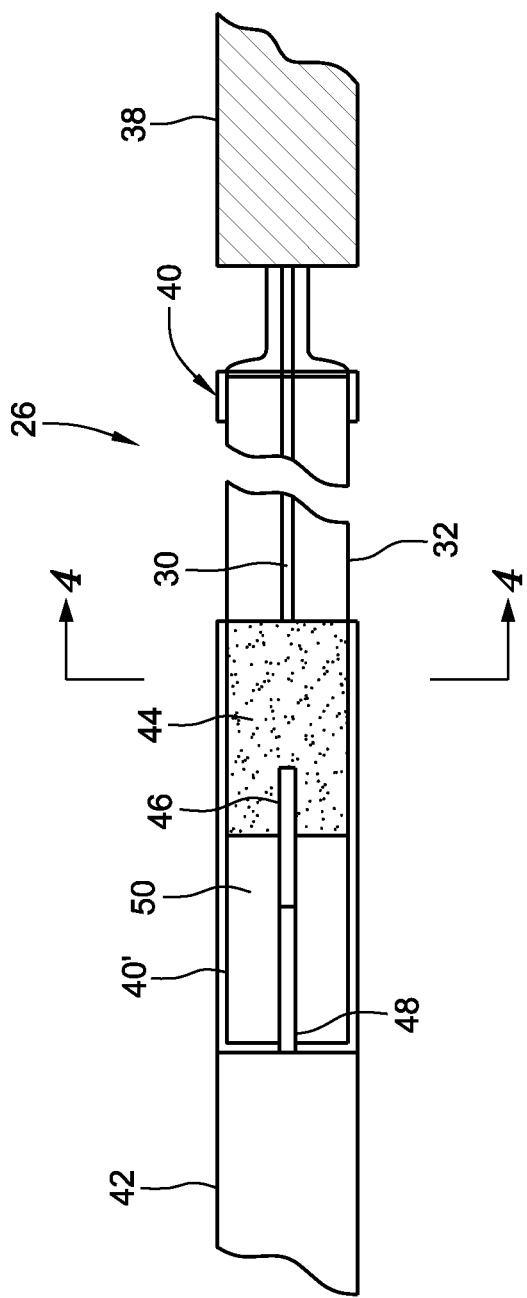
FIG. 2C is a fragmented plan view of the flat wire assembly of FIG. 2B showing the flat wire joined to the activation wire and the loop wire with the aid of soldering and adhesive, respectively.

FIG. 2B is a fragmented perspective view of flat wire assembly 26 of FIG. 2A showing flat wire 32 linking activation wire 30 and loop wire 48. FIG. 2C is a fragmented plan view of flat wire assembly 26 of FIG. 2B showing flat wire 32 joined to activation wire 30 and loop wire 48 with the aid of soldering 44 and adhesive 50, respectively. FIGS. 2B and 2C are discussed concurrently.

In one embodiment, activation wire 30 comprises a 300-series stainless steel. Loop wire 48, which may also comprise a length of 300-series stainless steel, such as 304 Vanadium stainless steel, is inserted into a distal end of tube 46. In another embodiment, loop wire 48 may comprise shape memory nitinol wire. A flattened proximal end of tube 46, which may be approximately 1 mm long, facilitates adhesion to flat wire 32 and soldering 44 with urethane adhesive 50 (or other suitable medical grade adhesive). Adhesive 50, soldering 44 and tube 46 are wrapped in polyimide tubing 40' for containment. Soldering 44 of connection device 28 metallurgically couples flat wire 32 and activation wire 30. A segment of polyimide tubing 40 filled with urethane adhesive 50 encapsulates the smaller diameter polyimide tubing 52 where the activation wire 30 resides, as well as polyimide tube 34 beneath flat wire 32. A gap G of about 1-2 mm between tubing 40 and the distal end of extended braid/spring subassembly 38 should be optionally maintained (as depicted). Activation wire 30 and conductor wires 36 (within polyimide tube 34) are conveyed through subassembly 38 to handle 22 or other remote location.

The application of force to activation wire 30 causes activation wire to slide within tubing 52 and deflect the distal portion of flat wire 32 via the connection devices described herein. Flat wire 32 acts as a spring to return catheter shaft 12 to a straight position when not subject to force or loading.

Figure 3:
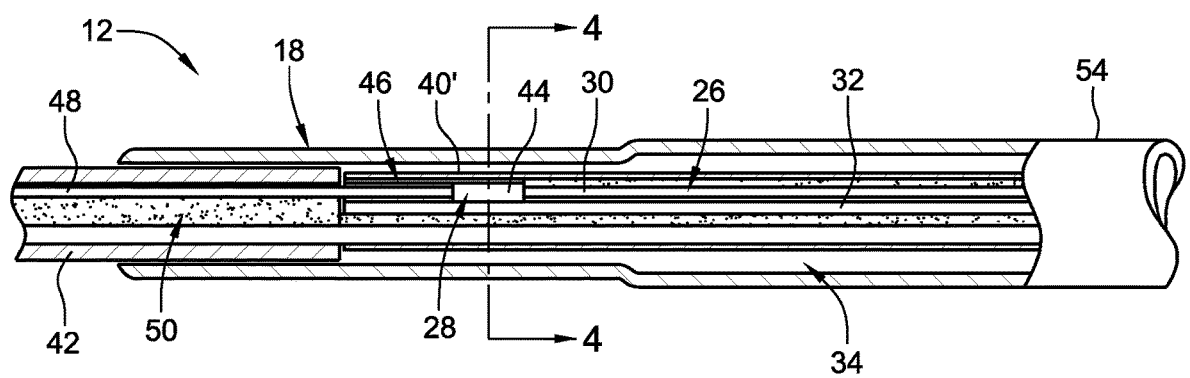
FIG. 3 is a side cross-sectional view of the catheter shaft of FIG. 1 showing the location of a connection device of the flat wire assembly joining the flat wire and the activation wire within soldering of a neck region of the shaft.

FIG. 3 is an elevational side view in partial cross section of neck region 18 formed just proximal of distal loop region 16 of the exemplary EP catheter 10 depicted in FIGS. 1A and 1B. FIG. 3 shows the location of connection device 28 of flat wire assembly 26 joining flat wire 32 and activation wire 30 within neck region 18. As shown, biocompatible tubing 42 of distal loop region 16 is surrounded by a smaller diameter portion of biocompatible tubing 54 of proximal shaft region 14 to form neck region 18. Neck region 18 transitions the outer diameter to about 4 F at distal loop region 16. Where neck region 18 terminates at its distal edge a small amount of medical grade adhesive polymer (e.g., such as used at the edges of electrodes 20) can be applied at the junction with biocompatible tubing 42. Polyimide tube 40' passes through neck region 18 to distal loop region 16 and isolates a plurality of elongate conductive strands 36 (within tube 34) that couple electrodes 20 and the tip electrode to remote circuitry via a handle 22 (as shown in FIGS. 1A and 1B) having a mass termination where conductors 36 pass through the handle to couple to an EP recording system or other diagnostic equipment, for example.

Figure 4:
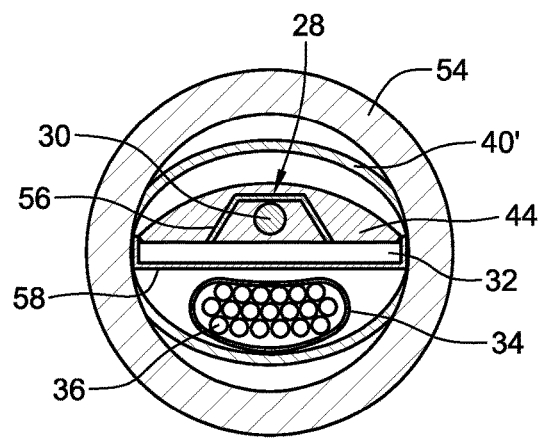
FIG. 4 is an axial cross-sectional view of the catheter shaft of FIG. 3 showing the flat wire having a detent for retaining the activation wire within soldering of the connection device.

Flat wire assembly 26, which includes flat wire 32 and connection device 28, is coupled to activation wire 30 and is adapted to impart and release tension to deflect distal loop region 16 in a plane defined by flat wire assembly 26 (via manipulation of handle 24, such as by rotation or linear actuation members, and the like). A short segment of polyimide tubing 40' surrounds a junction of several components; namely, tube 46 (e.g. a lubricous tubing member such as PEEK tubing) that receives a proximal end of loop wire 48 (formed of nitinol, for example) that is preformed into a desired dimension and configuration for distal loop region 16. At the junction of flat wire assembly 26 with loop wire 48 wrapped in, for example, PEEK tubing 46, urethane adhesive 50 can be applied between, above, and around the components within the polyimide tubing 40' to encapsulate same. Similarly, urethane adhesive 50 can be impregnated into the interstices of neck region 18 and distal loop region 16 to reduce or eliminate any migration of loop wire 48 or tube 46 or polyimide tube 34 (surrounding conductor 36) during use. Connection device 28 includes soldering 44 in order to facilitate connection of activation wire 30 with flat wire 32. As shown in FIG. 4, in one embodiment, connection device 28 further includes a detent within flat wire 32 that surrounds activation wire 30.

FIG. 4 is an axial cross-sectional view of catheter shaft 12 of FIG. 3 showing flat wire 32 having detent 56 to form connection device 28, which retains activation wire 30 while being disposed within soldering 44. In the embodiment of FIG. 4, flat wire 32 is disposed in shrink wrap 58 to provide a biocompatible sheathing. Conductors 36 extend along the underside of flat wire 32 within tube 34. Tube 34 and flat wire 32 are disposed within tube 40'. Tube 40' is surrounded by neck region 18 of biocompatible tubing 54.

Figure 5:
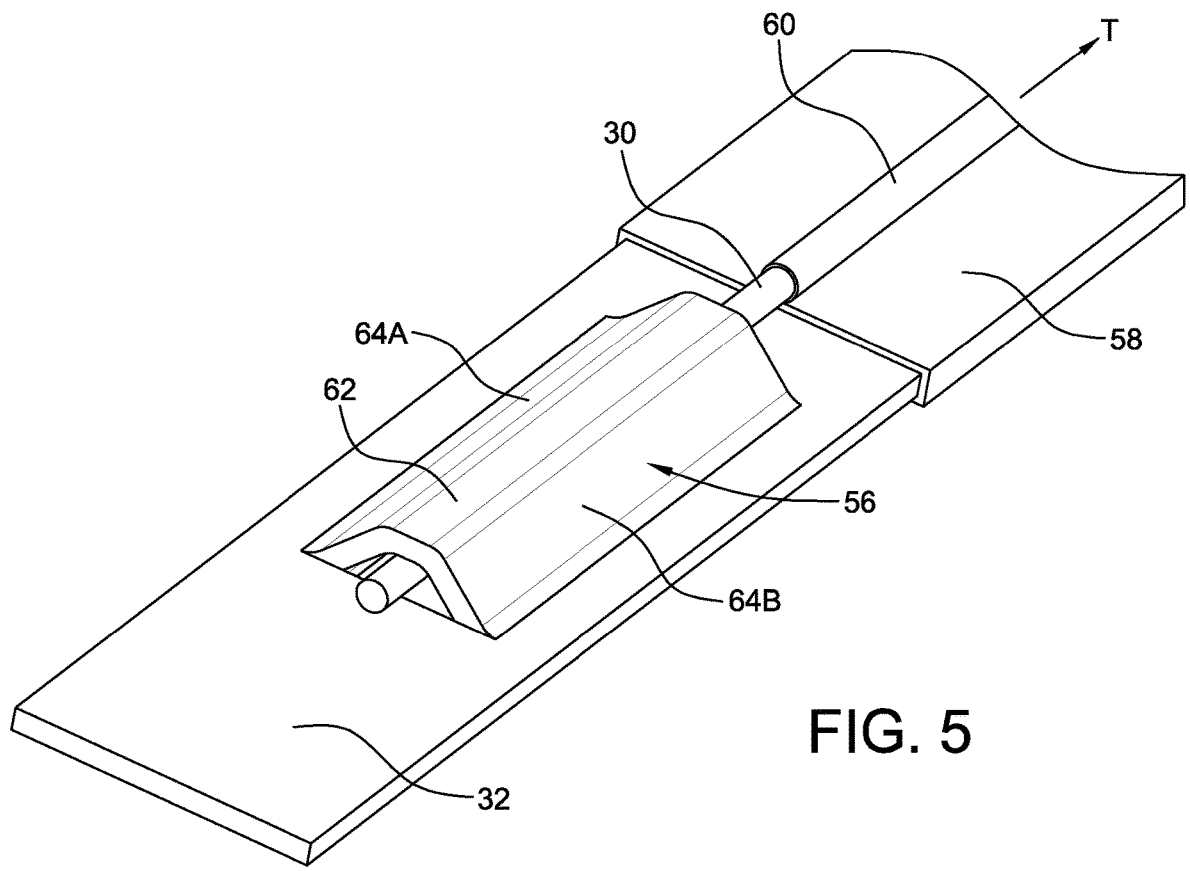
FIG. 5 is a perspective view of the flat wire of FIG. 4 showing the activation wire inserted into the detent of the connection device.

FIG. 5 is a perspective view of flat wire 32 of FIG. 4 showing activation wire 30 inserted into detent 56 of connection device 28. Portions of flat wire 32 may be encapsulated in shrink wrap 58, while portions of activation wire 30 may be sheathed in PTFE coating 60. In the disclosed embodiment of FIG. 5, detent 56 comprises a three-sided slot having end surface 62 and side surfaces 64A and 64B. Sides 62, 64A and 64B form a passage through flat wire 32. Specifically, sides 62, 64A and 64B form an elongated slot along flat wire 32 into which activation wire 30 is inserted. In the depicted embodiment, sides 62, 64A and 64B are flat.

In other embodiments, detent 56 may have a V-shape where the width of end surface 62 is de minimis. In yet other embodiments, detent 56 may have a rectangular, or curved or arcuate shape that forms a single smooth surface extending over activation wire 30.

A bonding agent, such as soldering 44, is applied over the interface between activation wire 30 and flat wire 32. Specifically, the slot formed by detent 56 forms a trough filled by the bonding agent. With such a configuration, the strength of the material of flat wire 32 is used in addition to the strength of the bonding agent to hold activation wire 30 in engagement with flat wire 32.

As activation wire 30 is subject to tensile force T from handle 24 (FIG. 1A), for example, out-of-plane forces are generated such that flat wire 32 flexes and space is generated between activation wire 30 and flat wire 32. As such, a peeling force is generated as activation wire 30 tends to peel away from flat wire 32. Detent 56 extends portions of flat wire 32 around the top (with reference to the orientation of FIG. 5) of activation wire 30 to directly counteract the peeling force generated during deflection of catheter 12. Due to the dissimilar shape of a round activation wire and a flat deflection/planarity wire, it is difficult to achieve a joint between activation wire 30 and flat wire 32 that is strong enough to withstand the forces applied to activation wire 30 with the sole means of a bonding agent, such as soldering.

The strength of the bonding agent, such as soldering 44, is typically much less than the strength of flat wire 32. For example, in one embodiment, activation wire 30 is fabricated from ninety-five percent cold worked 304 Vanadium steel, and flat wire 32 is fabricated from heat treated 17-7 stainless steel. With such a combination, a tin-based, lead-free soldering paste may be used. The yield strength of such a soldering paste is approximately 8,000 pounds per square inch (psi) [~55.2 MPa] to approximately 10,000 psi [~68.9 MPa]. The yield strength of heat treated 17-7 stainless steel is approximately 65,000 psi [~448 MPa]. Thus, in the embodiment of FIG. 5, the material of flat wire 32 is wrapped over activation wire 30 to use the available strength of the flat wire to directly counteract the peeling force. Activation wire 30 is circumferentially surrounded by portions of flat wire 32 to react forces in all different directions.

Figure 6:
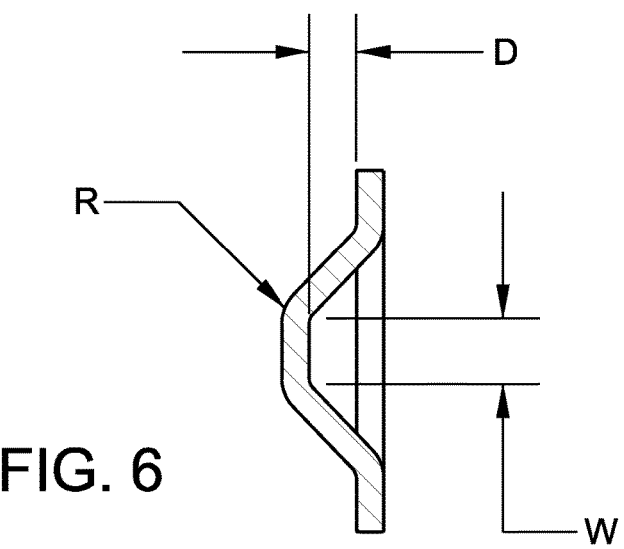
FIG. 6 is an axial cross-sectional view of the detent of FIG. 5 showing the geometry of the detent.

FIG. 6 is an axial cross-sectional view of detent 56 of FIG. 5 showing the geometry of detent 56. In the depicted embodiment, detent 56 forms a trough or slot having a depth D of approximately 0.0085 inches [~0.22 mm], and a width W of approximately 0.012 inches [~0.30 mm], with a radius R of approximately 0.005 inches [~0.13 mm] The dimensions of detent 56, in the depicted embodiment, are selected for activation wire 30 having a diameter of approximately 0.007 inches [~0.18 mm] The sloped walls of detent 56 assist in controlling solder volume. Detent 56 can be formed by stamping or punching a die into flat wire 32. The process for forming detent 56, soldering 44 (FIG. 4) and the resulting formation of connection device 28 is discussed with reference to FIGS. 7A-7G.

In addition to the embodiment depicted in FIG. 6, other embodiments can include any dimensions for the depth D, width W, and radius R of detent 56. For example, the width W of detent 56 could be greater than 0.012 inches, so as to provide a greater area of flat wire 32 to counteract the peeling force. In another example, two separate detents could be formed around activation wire 30, with an open space in between the detents. Thus, various combinations of detent structure and shape can be used provide maximal resistance to the peeling force.

Figure 7A:
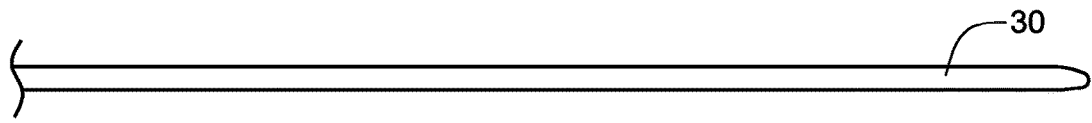
FIGS. 7A-7G are schematic illustrations showing the steps of producing a connection device according to a soldered detent method.
Figure 7B:
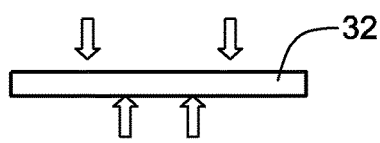
Figure 7C:
Figure 7D:
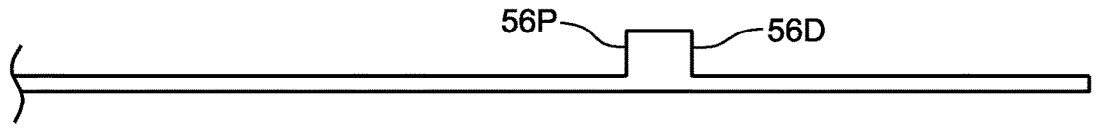
Figure 7E:
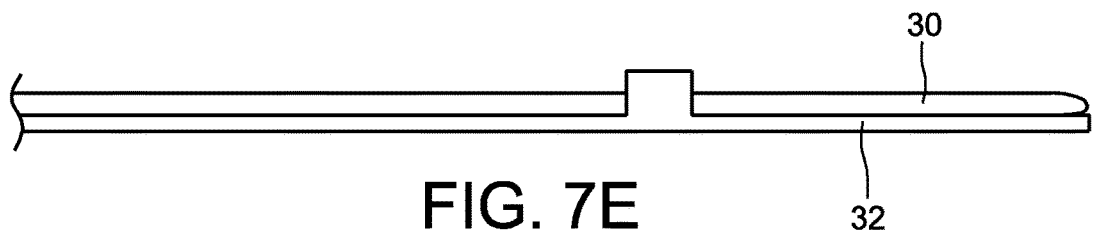
Figure 7F:
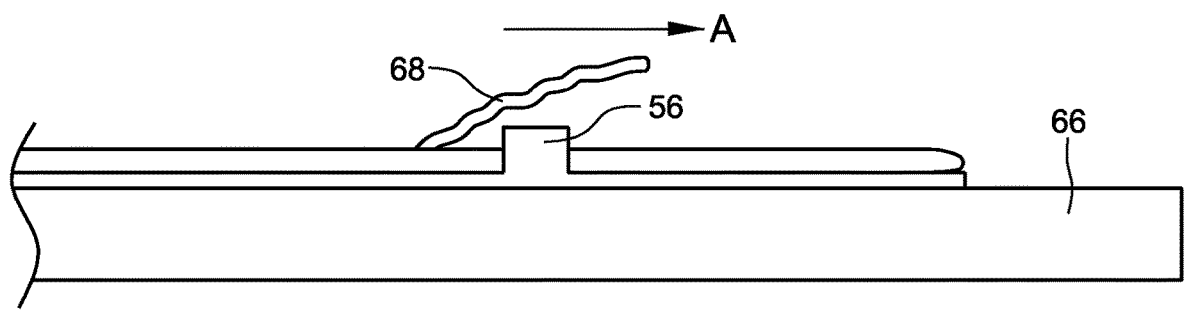

FIGS. 7A-7G are schematic illustrations showing the steps of producing connection device 28 according to a soldered detent method. FIGS. 7A-7G are for illustrative purposes and are not drawn to scale. Connection device 28 includes detent 56 and soldering 44, as can be seen in FIG. 7F.

FIG. 7A shows a side view of activation wire 30 as produced from 0.007 inch [~0.18 mm] diameter 304 Vanadium stainless steel. Although, activation wire 30 may have other diameters, such as 0.0065 inch [~0.17 mm] and 0.0075 inch [~0.19 mm], and be made from other materials. The distal end of activation wire 30 shown in FIG. 7A is prepped for soldering by removing coatings, such as PTFE coating 60 (FIG. 5). Additionally, in various embodiments, the stripped end of activation wire 30 may be roughened using any conventional technique, such as grit blasting, to facilitate bonding with soldering 44.

FIG. 7B shows an axial end view of flat wire 32 as produced from 17-7 stainless steel and having a width of approximately 0.0661 inches [~1.68 mm] and a thickness of approximately 0.005 inches [~0.127 mm] Detent 56 is produced by subjecting flat wire 32 to a "punch" force, as shown in FIG. 7B. In one embodiment, conventional 4-slide tooling equipment and processes are used to form detent 56. Additionally, in various embodiments, flat wire 32 may be roughened using any conventional technique, such as grit blasting, to facilitate bonding with soldering 44. The area where flat wire 32 is "punched" to form detent 56 can be sized (e.g., widened) to avoid dimensional changes, such as narrowing or "pull-in", for example, of the flat wire 32 after punching.

FIG. 7C shows an axial end view of detent 56 forming a three-sided V-shaped channel. Although, as described above, detent 56 may have other profiles, such as rectangular or arcuate. In the depicted embodiment, detent 56 has a depth of approximately 0.008 inches [~0.20 mm] The diameter of activation wire 30 and the depth of detent 56 may be selected to provide an interference fit to provide a mechanical interface that further couples and strengthens the connection with flat wire 32.

FIG. 7D shows a side profile of flat wire 32 with detent 56 completely formed. In one embodiment, detent 56 has a width of approximately 0.1168 inches [~2.97 mm] In order to facilitate punching or pressing of detent 56, flat wire 32 may be provided with relief cut-outs, e.g. slots, at proximal and distal ends 56P, 56D of detent 56 before detent 56 is shaped.

FIG. 7E shows activation wire 30 as inserted into detent 56. Activation wire 30 is shown extending through detent 56 to near the distal end of flat wire 32, but need not extend that far in other embodiments. Activation wire 30 extends far enough past detent 56 to ensure soldering 44 will completely envelop the engagement of activation wire 30 and detent 56. Excess length of activation wire 30 remaining after soldering may be removed, if desired.

FIG. 7F shows resistance heater 66 disposed underneath flat wire 32 with solder paste 68 disposed above detent 56. Solder paste 68 is applied to detent 56 in direction D extending from the proximal end toward the distal end of flat wire 32. Solder paste 68 may be applied over a length of approximately 0.118 inches [~3.0 mm] In any particular embodiment, solder paste 68 may comprise any suitable solder paste for the given materials of flat wire 32 and activation wire 30. In various embodiments, solder paste 32 comprises lead-free pastes, such as pure Sn, Sn-3.5Ag, Sn-5Ag, Sn-3Cu, and Sn-5Sb. Resistance heater 66 may comprise any suitable resistance heater capable of heating solder paste 68 to its reflow temperature. In other embodiments, other types of heating devices may be used to bring solder paste 68 to the reflow temperature. In one embodiment, resistance heater 66 heats solder paste 68 above the reflow temperature to ensure solder paste 68 flows into the spaces between activation wire 30 and detent 56.

Figure 7G:
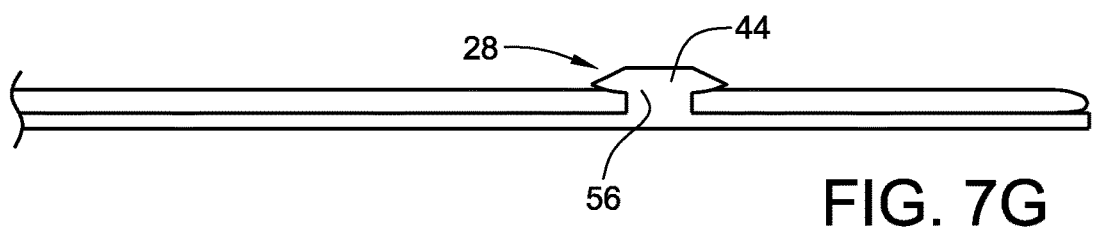

FIG. 7G shows the completion of connection device 28. Heated solder paste 44 flows into the spaces of detent 56 surrounding activation wire 30 and into the pores of activation wire 30 and flat wire 32, thereby forming a metallurgical bond or interface. The sloped walls of detent 56 (e.g. sides 64A and 64B of FIG. 5) help provide proper solder volume as soldering 44 fills in underneath detent 56. As such the slope of the walls can be altered and selected to influence the volume of solder that enters detent 56 for a given design. Solder paste 68 may be applied to form soldering having a depth of approximately 0.02 inches [~0.51 mm], with activation wire being disposed as close to flat wire 32 a possible.

Although FIGS. 7A-7G are described with respect to soldering, other types of bonding agents can be used. For example, welding, brazing or adhesives may be used to enhance the interface bond between activation wire 30, flat wire 32 and detent 56.

As mentioned, the metallurgical bond or interface can be enhanced with mechanical interface means, such as an interference fit between activation wire 30 and detent 56. Additional mechanical interface means, such as coining, can be used in addition to or in lieu of soldering 44.

Figure 8A:
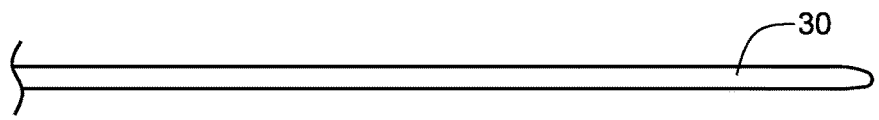
FIGS. 8A-8H are schematic illustrations showing the steps of producing a connection device according to a coined detent method.
Figure 8B:
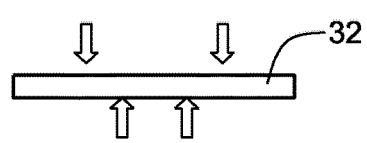
Figure 8C:
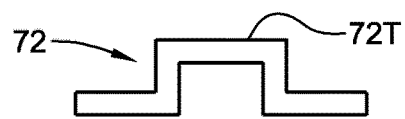
Figure 8D:
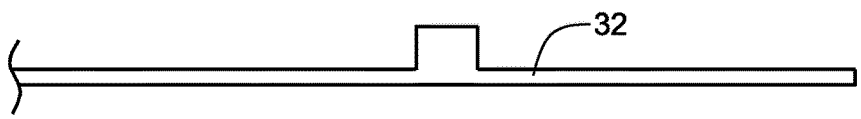
Figure 8E:
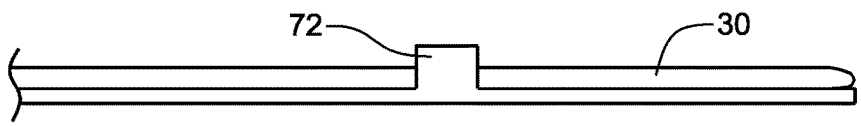
Figure 8F:
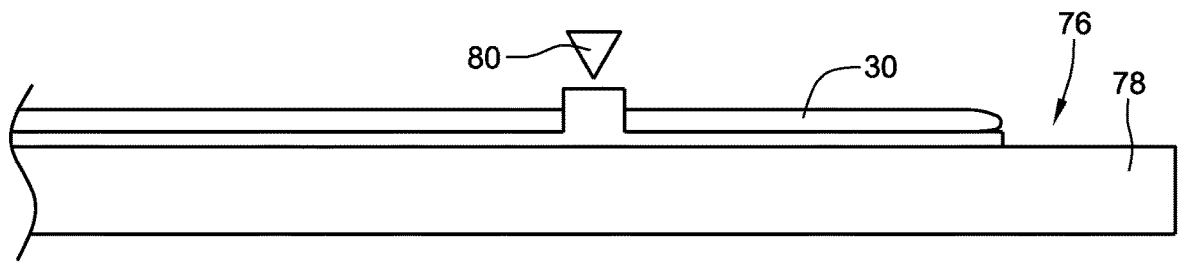
Figure 8G:
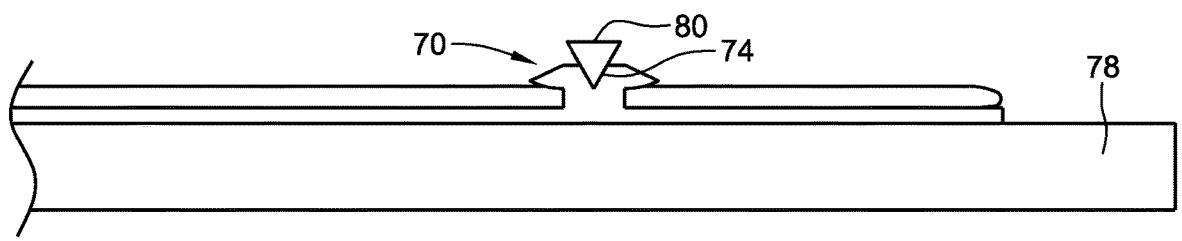
Figure 8H:
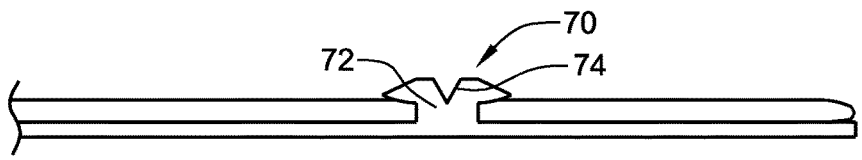

FIGS. 8A-8H are schematic illustrations showing the steps of producing connection device 70 according to a coined detent method. FIGS. 8A-8H are for illustrative purposes and are not drawn to scale. Connection device 70 includes detent 72 and coining 74, as can be seen in FIG. 8H.

FIGS. 8A-8E show similar steps as are described with reference to FIGS. 7A-7E. Thus, the description provided above additionally applies to FGIS. 8A-8E. However, FIGS. 8A-8E show detent 72 having a three-sided rectangular shape. Both the height and width of detent 72 may be approximately 0.008 inches [~0.203 mm] Other shaped detents, such as V-shaped, arcuate or square-shaped, work with the described coining method of FIGS. 8A-8H. In any embodiment of detent 72, the depth (e.g. depth D of FIG. 6) is kept small so as to facilitate the coining process. In particular, it is desirable that top surface 72T be maintained close to or in contact with activation wire 30 (as shown in FIG. 8E) to ensure that material of flat wire 32 is adequately pushed into the material of activation wire 30 with the coining process.

FIG. 8F shows activation wire 30 inserted into detent 72, with flat wire 32 disposed on coining tool 76, which includes base 78 and mandrel 80. Base 78 provides a flat surface to support flat wire 32 and to react the forces generated by mandrel 80. Mandrel 80 comprises a pointed or sharpened object that can be moved downward toward base 78 with force. Coining tool 76 may comprise any suitable coining system as is known in the art.

FIG. 8G shows detent 72 disposed between mandrel 80 and base 78, and mandrel 80 moved toward detent 72 to push top surface 72T into activation wire 30. Top surface 72T and activation wire 30 are mechanically deformed such that material of detent 72 is pushed into a dent or divot within activation wire 30 to form coining 74. As such, a mechanical interface is formed between detent 72 and activation wire 30.

FIG. 8H shows coining 74 formed into detent 72. As a result of the coining process, material of detent 72 is pushed proximally and distally from coining 74 to form connection device 70. In some embodiments, a bonding process can be used to further secure activation wire 30 with respect to flat wire 32. For example, activation wire 30 can be welded, brazed, soldered or glued to flat wire 32.

FIGS. 7A-7G and 8A-8H describe methods of producing connection devices that involve producing passages that result in elongate slots or channels along flat wire 32 such that activation wire 30 remains disposed along one side of flat wire 32. Such methods effectively utilize the strength of flat wire 32 in securing activation wire 30. Such methods are also effective in minimizing the height of the connection device, which helps in maintaining a small diameter so that the connection device can be readily disposed in catheter shaft 12. Additionally, such methods increase the length of the interface between activation wire 30 and flat wire 32, thereby providing additional space for the formation of a metallurgical interface or bond. Also, the elongate slots of such methods produce troughs having wall shapes and geometries that can help control solder volume. In other embodiments, passages can be produced that allow activation wire to pass through flat wire 32 so as to be disposed on both sides of flat wire 32 and thereby form a hooked interface.

Figure 9A:
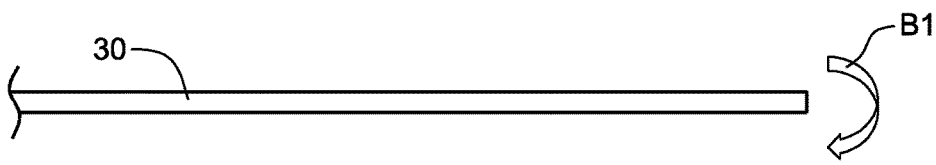
FIGS. 9A-9G are schematic illustrations showing the steps of producing a connection device according to a soldered Z-hook method.
Figure 9B:
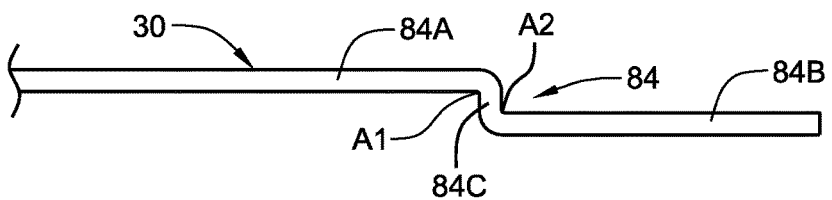
Figure 9C:
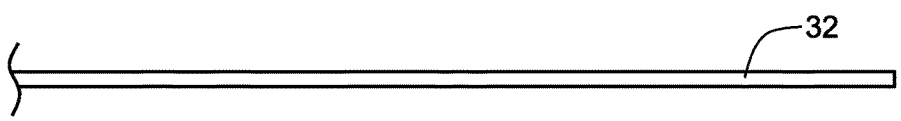
Figure 9D:
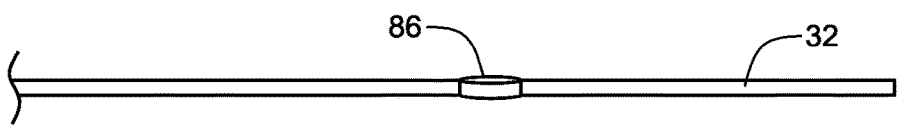
Figure 9E:
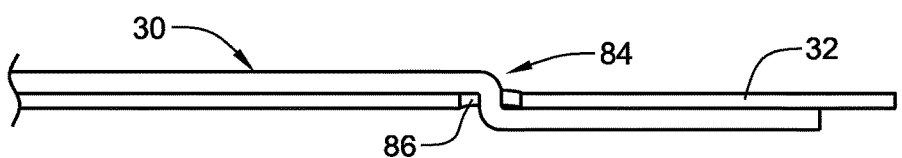
Figure 9F:
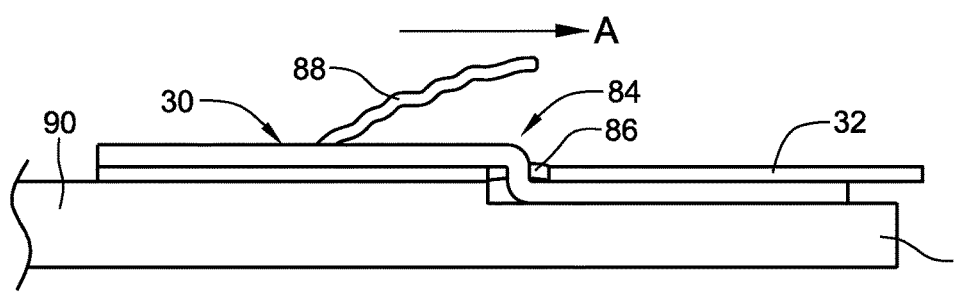

FIGS. 9A-9G are schematic illustrations showing the steps of producing connection device 82 according to a soldered Z-hook method. FIGS. 9A-9G are for illustrative purposes and are not drawn to scale. Connection device 82 includes Z-hook 84, bore 86 and solder paste 88, as can be seen in FIG. 9F.

FIG. 9A shows a distal end of activation wire 30 being subject to bending force B1. Bending force B1 can be generated by any suitable means. Conventional 4-slide tooling equipment and processes may be used to form Z-hook 84. Activation wire 30 may comprise similar characteristics as described with reference to FIG. 7A.

FIG. 9B shows Z-hook 84 having first and second lateral legs 84A and 84B, and transverse leg 84C. In the disclose embodiment, Z-hook 84 includes two right angle bends at A1 and A2. However, in other embodiments larger angles can be used at A1 and A2 to provide activation wire with a shallower jog. For example, activation wire 30 can include one-hundred-twenty-degree angles at A1 and A2. In one embodiment, second lateral leg 84B has a length of approximately 0.118 inches [~3.0 mm].

FIG. 9C shows a side view of the distal end of flat wire 32. Flat wire 32 may comprise similar characteristics as described with reference to FIG. 7B.

FIG. 9D shows a passage in the form of bore 86 extending radially through flat wire 32 from one side to the other. In the disclosed embodiment, bore 86 has a diameter of approximately 0.008 inches [~0.20 mm] for activation wire 30 having a diameter of approximately 0.007 inch [~0.18 mm] diameter. Thus, bore 86 is approximately 0.001 inch [~0.0254 mm] larger than the diameter of activation wire 30 to allow activation wire to pass therethrough, but to provide a tight mechanical fit. Bore 86 may be produced with any suitable means, such as a carbide drill or laser drilling, with laser drilling being preferred to reduce burring.

FIG. 9E shows activation wire 30 interweaved with flat wire 32 such that transverse leg 84C of Z-hook 84 engages with bore 86. As shown, first lateral leg 84A is disposed on the top of flat wire 32, while second lateral leg 84B is disposed on the bottom of flat wire 32 (with reference to the orientation of FIG. 9C). Disposed as such, activation wire 30 is mechanically interlocked with flat wire 32.

FIG. 9F shows resistance heater 90 disposed underneath flat wire 32 with solder paste 88 disposed above Z-hook 84.

Resistance heater 90 includes slot 92 into which lateral leg 84B is disposed so that flat wire 32 may lie substantially flat atop resistance heater 90. Solder paste 88 is applied over bore 86 and transverse leg 84C in direction A. Resistance heater 90 is operated similarly as is described with reference to FIG. 7F to achieve proper melting of solder paste 88 into the spaces between bore 86 and transverse leg 84C.

Figure 9G:
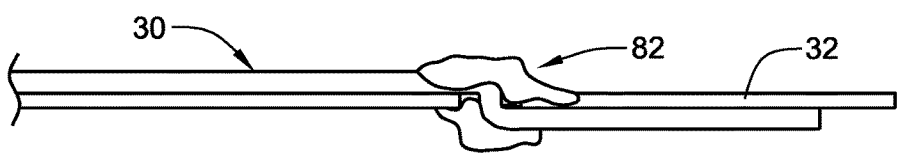

FIG. 9G shows soldering paste 88 being applied on first lateral leg 84A and transverse leg 84C. Solder paste 88 melts into the spaces surrounding transverse leg 84C and bore 86 in order to form connection device 82. As such, soldering is present on both sides of flat wire 32. In other embodiments, soldering paste 88 may be initially applied to second lateral leg 84B, or both lateral legs 84A, 84B. In one embodiment, sufficient solder paste 88 is used to that the thickness of soldering on either side of flat wire 32 is in the range of approximately 0.002 inches [~0.051 mm] to approximately 0.016 inches [~0.406 mm].

The engagement of activation wire 30 with bore 86 allows for connection device 82 to more effectively utilize the strength of activation wire 30. Specifically, transverse leg 84C directly engages flat wire 32 at bore 86 when tensile force is applied to lateral leg 84A. Additionally, as activation wire 30 separates from flat wire 32 under stress, lateral leg 84B resists the peeling forces generated between lateral leg 84B and flat wire 32. Connection device 82 additionally provides increased surface area, such as at bore 86, for improving metallurgical bonding with solder paste 88.

Figure 10A:
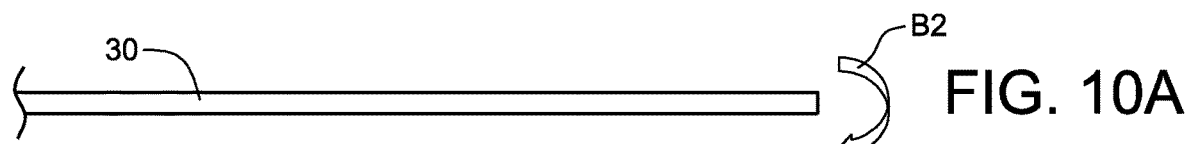
FIGS. 10A-10H are schematic illustrations showing the steps of producing a connection device according to a soldered J-hook method.
Figure 10B:
Figure 10C:
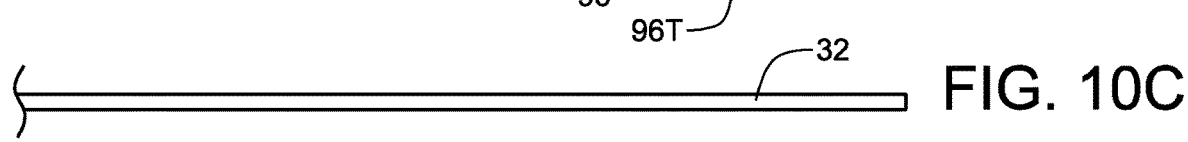
Figure 10D:
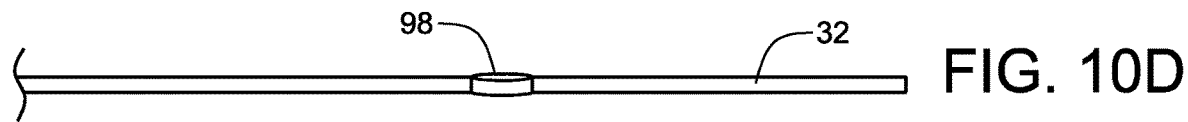
Figure 10E:
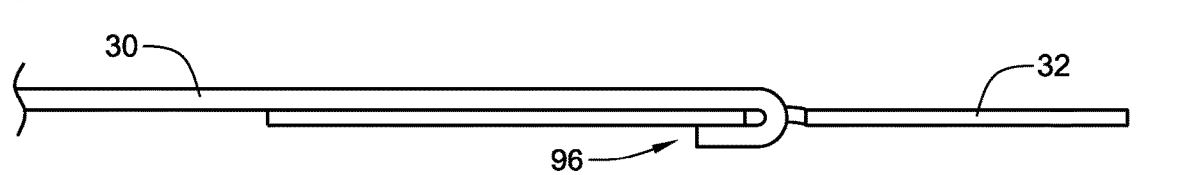
Figure 10F:
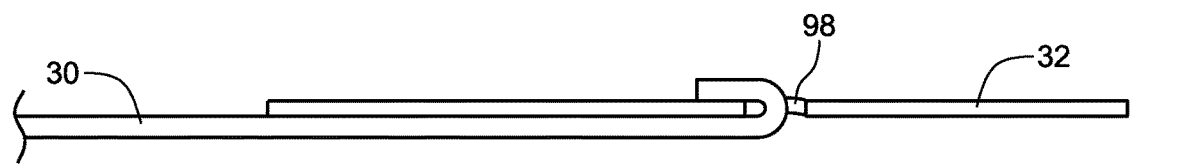
Figure 10G:
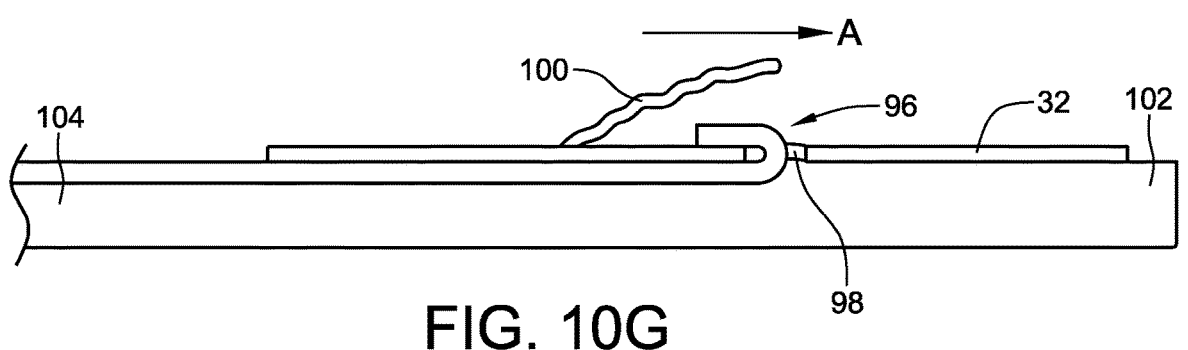
Figure 10H:

FIGS. 10A-10H are schematic illustrations showing the steps of producing connection device according to a soldered J-hook method. FIGS. 10A-10H are for illustrative purposes and are not drawn to scale. Connection device 94 includes J-hook 96, bore 98 and solder paste 100, as can be seen in FIG. 10G.

FIGS. 10A-10H describe a process substantially similar to that of FIGS. 9A-9G, with the main difference being the shape of J-hook 96, which results in resistance heater 90 having slightly different shape at slot 104. Additionally, the formation of soldering from solder paste 100 has a different flow dynamic than solder paste 88 of FIG. 9F due to the difference in geometry of J-hook 96 and bore 98.

FIG. 10B shows J-hook 96 having a radius at location L so that J-hook 96 includes tail 96T. In various embodiments, tail 96T may have a length in the range of approximately 0.059 inches [~1.5 mm] to approximately 0.118 inches [~3.0 mm] In the disclose embodiment, J-hook 96 has a radius slightly larger than approximately half the thickness of flat wire 32 to allow J-hook 96 to tightly wrap around bore 98. A small radius at location L is desirable to increase the mechanical coupling, but is undesirable due to increased difficulty in navigating activation wire 30 through bore 98 and higher bending stresses induced in activation wire 30. Thus, in other embodiments, a larger radius can be used at location L to reduce stress and increase maneuverability.

FIG. 10G shows resistance heater 102 disposed underneath flat wire 32 (with reference to the orientation of FIG. 10G) with solder paste 100 disposed above J-hook 96. First, however, the assembly of flat wire 32 and activation wire 30 is flipped upside down (as shown in FIG. 10F) so that solder paste 100 is applied to the underside of flat wire 32 across tail 96T. Resistance heater 102 includes slot 104 into which activation wire 30 is disposed so that flat wire 32 may lie substantially flat across resistance heater 90 and activation wire 30. Solder paste 100 is applied over bore 98 and tail 96T in direction A. Resistance heater 102 is operated similarly as is described with reference to FIG. 7F to achieve proper melting of solder paste 100 into the spaces between bore 98 and J-hook 96. Due to the tight fit between J-hook 96 and bore 98, a minimal amount of soldering paste 100 passes through bore 98. Soldering is performed at tail 96T so as to allow activation wire 30 to flex under peeling forces to transfer the tensile forces directly to the engagement between bore 98 and J-hook 96.

As with the Z-hook embodiment of FIGS. 9A-9G, J-hook 96 allows for more effective use of the tensile strength of activation wire 30. Specifically, location L directly engages flat wire 32 at bore 98 when tensile force is applied to activation wire 30. Additionally, as activation wire 30 separates from flat wire 32 under stress, tail 96T resists the peeling forces generated between activation wire 30 and flat wire 32. Connection device 94 additionally provides increased surface area, such as at bore 98, for improving metallurgical bonding with solder paste 100.

The connection devices of the present disclosure are able to withstand significantly higher loads than conventional solder-only joints. Studies have shown that solder-only joints, where a round activation wire is laid flat against a flat wire and soldered, fail at peel forces of approximately 7 lbf [~31.1 N], even though the activation wire can withstand tensile loading of approximately 13 lbf [~57.8 N]. With the connection devices of the present disclosure, activation wires fail at approximately 10 lbf [~44.5 N], much closer to the tensile strength of the activation wire of 13 lbf [~57.8 N].

Figure 11:
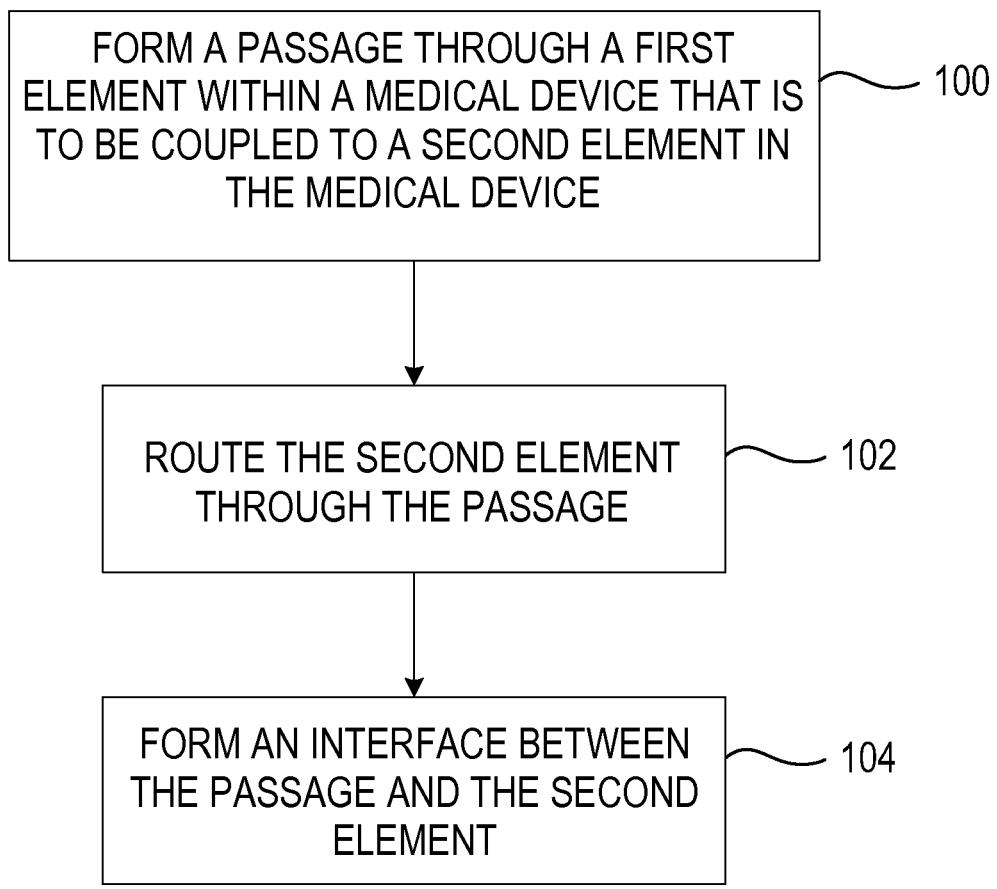
FIG. 11 is a block diagram illustrating a method for manufacturing a connection between at least two different elements in a medical device.

FIG. 11 is a block diagram illustrating a method for manufacturing a connection between at least two different elements in a medical device. Apparatuses and systems according to the disclosure may be manufactured to incorporate the features described herein or combinations thereof using various embodiments of the methods described herein.

In one embodiment, such a method may involve forming 100 a passage, such as a hole, slot, groove, detent, channel, or other passage, in a first element that facilitates interaction with a second element. The forming may be executed with mechanical drilling, laser drilling, punching, bending, etching, or any other suitable means. The second element may be routed 102 through or along the passage formed in the first element. In exemplary embodiments, the routing may result in the second element being disposed substantially parallel to the first element at the passage, or being substantially angled relative to the first element at the passage. An interface may be formed 104 between the passage and second element. In exemplary embodiments, the interface may include mechanical and/or metallurgical coupling means, such as hooking, interconnecting, coining, crimping, soldering, brazing, welding and the like.

Such a method of manufacturing may be used to facilitate, for example, the connection of dissimilar geometric elements within a medical device such as a catheter, introducer, etc. In one embodiment, the first element may be a pull ring or other connection member to which a second element, such as a steering/pull wire, may be connected. In such an example, a passage may be formed 100 through the pull ring, the pull wire may be routed 102 through the passage in the pull ring, and an interface may be formed 104 between the pull ring passage and the pull wire.

In another representative embodiment, a method for manufacturing a connection device between a flat wire and a round wire in a medical device is provided, where a passage is formed 100 within a flat wire, a round wire is fed or otherwise routed 102 through the passage, and an interface is formed 104 between the passage and the round wire. In representative embodiments, the passage may be created by forming a channel across one side of the flat wire, or forming a bore through the flat wire from one side to an opposite side, or the like. A portion of the flat wire forming the passage and a portion of the round wire in the passage may be coined to assist with the interface. In other embodiments where a bore is made through the flat wire, a portion (e.g., end portion) of the round wire may be shaped appropriately to engage with the bore and, among other things, facilitate the structural integrity of the interface. In other embodiments, the interface may be provided with metallurgical bonding, such as soldering, brazing, welding and the like.

Various embodiments are described herein to various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments.

Although a number of embodiments have been described above with a certain degree of particularity, those skilled in the art could make numerous alterations to the disclosed embodiments without departing from the sprit or scope of this disclosure. For example, all joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure.

Any patent, publication, or other disclosure material, in whole or in part, that is said to be incorporated by referenced herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation given that such combination is not illogical or non-functional.

What is claimed is:

1. A connection device for a deflectable catheter, the connection device comprising:
   an elongate flat wire having a proximal end and a distal end, the wire configured to effect deflection of the catheter within a single plane;
   an elongate activation wire having a proximal end a distal end;
   a passage extending through the flat wire near the distal end of the flat wire, wherein the distal end of the activation wire extends through the passage; and
   an interface between the passage and the activation wire;
   wherein the passage comprises an elongate slot extending axially along a surface of the flat wire, the elongate slot comprising a proximal end opening and a distal end opening;
   wherein the activation wire extends through both the proximal end opening and the distal end opening;
   wherein the elongate slot comprises a detent extending out of the surface of the flat wire such that the activation wire extends straight between the detent and the flat wire;
   wherein the interface includes a bonding agent joining the activation wire to the flat wire at the passage; and
   wherein the detent retains the activation wire within the interface.

2. The connection device of claim 1, wherein the interface is mechanically deformed to produce a mechanical engagement between the flat wire and the activation wire.

3. The connection device of claim 1, wherein the interface includes metallurgical bonding between the flat wire and the activation wire.

4. The medical device of claim 1 wherein said detent comprises v-shaped trough indented into the flat wire.

5. The medical device of claim 1 wherein the flat wire is mechanically deformed at the passage to engage the activation wire.

6. The medical device of claim 5 wherein said mechanical deformation comprises a coining of said slot.

7. The connection device of claim 1 wherein said bonding agent is selected from the group consisting of solder, weld, braze, and adhesive.

8. A method for manufacturing a connection device between a flat wire and a round wire in a medical device, the method comprising:
   forming a passage within a flat wire;
   feeding a round wire through the passage; and
   forming an interface between said passage and said round wire;
   wherein the passage comprises an elongate slot extending axially along a surface of the flat wire, the elongate slot comprising a proximal end opening and a distal end opening;
   wherein the round wire extends through both the proximal end opening and the distal end opening;
   wherein the elongate slot comprises a detent extending out of the surface of the flat wire such that the round wire extends straight between the detent and the flat wire;
   wherein the interface includes a bonding agent joining the round wire to the flat wire at the passage; and
   wherein the detent retains the round wire within the interface.

9. The method of claim 8, wherein forming said passage comprises forming a channel across one side of said flat wire.

10. The method of claim 9, further comprising coining a portion of said flat wire forming said passage and a portion of said round wire in said passage.

\* \* \* \* \*